US00PP26721P3

(12) United States Plant Patent
Klemm et al.

(10) Patent No.: US PP26,721 P3
(45) Date of Patent: May 10, 2016

(54) ***DIANTHUS* PLANT NAMED 'KLEDP13155'**

(50) Latin Name: *Dianthus caryophyllus*
Varietal Denomination: KLEDP13155

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 112 days.

(21) Appl. No.: 14/120,255

(22) Filed: May 13, 2014

(65) Prior Publication Data

US 2015/0334896 P1 Nov. 19, 2015

(51) Int. Cl.
*A01H 5/02* (2006.01)

(52) U.S. Cl.
USPC ..... Plt./278

(58) Field of Classification Search
USPC ..... Plt./278, 273
See application file for complete search history.

*Primary Examiner* — Susan McCormick Ewoldt
(74) *Attorney, Agent, or Firm* — James M. Weatherly; Bethany R. Roahrig; Cochran Freund & Young, LLC

(57) ABSTRACT

A new *Dianthus* plant particularly distinguished by having double flowers with a stable, shiny red flower color, good branching, and strong vigor, is disclosed.

1 Drawing Sheet

Genus and species: *Dianthus caryophyllus*.
Variety denomination: 'KLEDP13155'.

BACKGROUND OF THE NEW PLANT

The present invention comprises a new and distinct variety of *Dianthus*, botanically known as *Dianthus caryophyllus* and hereinafter referred to by the variety name 'KLEDP13155'. 'KLEDP13155' is a selection that results from a cross pollination of the proprietary female *dianthus* line 'DCP 2007 0056' (unpatented) and the male *dianthus* line 'Fire' (patent status unknown).

In May of 2009 the proprietary female *dianthus* line 'DCP 2007 0056' and the male *dianthus* line 'Fire' were cross pollinated in Stuttgart, Germany and seeds were obtained. The seeds were sown and plants were grown for evaluation. A plant line was selected in June 2010 in Stuttgart, Germany, and named 'KLEDP13155'. In June 2010, 'KLEDP13155' was first vegetatively propagated by vegetative cuttings. 'KLEDP13155' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Double flowers with a stable, shiny red flower color;
2. Good branching; and
3. Strong vigor.

CROSS REFERENCE TO RELATED APPLICATIONS

Plant Breeder's Rights for 'KLEDP13155' were applied for in Canada on Jan. 20, 2014, application number 14-8175 and in Europe with the Community Plant Variety Office on Jun. 28, 2013, application number 2013/1747. 'KLEDP13155' has not been made publicly available or sold more than one year prior to the filing date of this application.

DESCRIPTION OF THE PHOTOGRAPH

This new *Dianthus* plant is illustrated by the accompanying photograph which shows an overall view of the plant. The colors shown are as true as can be reasonably obtained by conventional photographic procedures. The plant is about 5 months-old grown in Stuttgart, Germany in May 2012.

DESCRIPTION OF THE NEW VARIETY

The following detailed descriptions set forth the distinctive characteristics of 'KLEDP13155'. The data which define these characteristics were collected from asexual reproductions carried out in Stuttgart, Germany. Data was collected on five month-old plants grown in a greenhouse in Stuttgart, Germany in February 2014. Plants were pinched one time with a growth regulator. Color references are to The R.H.S. Colour Chart of The Royal Horticultural Society of London (R.H.S.), $5^{th}$ edition (2007).

Classification:
- *Family*.—Caryophyllaceae.
- *Species*.—*Dianthus caryophyllus*.
- *Common name*.—Pot carnation.
- *Variety*.—'KLEDP13155'.

Parentage:
- *Female*.—The proprietary *dianthus* 'DCP 2007 0056'.
- *Male*.—'Fire'.

Propagation:
- *Type*.—Vegetative cuttings.
- *Time to produce a rooted young plant*.—14 to 16 days.
- *Root description*.—White, fine.
- *Rooting habit*.—Lanceolate.

Plant description:

*Plant form*.—Potted plant, upright.

*Plant height*.—17.0 cm to 19.0 cm.

*Plant diameter or spread*.—14.0 cm to 16.0 cm.

Lateral branches:

*General description*.—Stem is solid.

*Length*.—9.0 cm.

*Diameter*.—5.0 cm.

*Internode length*.—1.5 cm to 2.0 cm.

*Average number of internodes per stem*.—4.

*Node length*.—0.4 cm.

*Node diameter*.—0.3 cm.

*Texture*.—Smooth.

*Color*.—RHS 137A.

Foliage description:

*Arrangement*.—Opposite.

*Length*.—6.0 cm to 8.0 cm.

*Width*.—0.7 cm.

*Shape*.—Lanceolate.

*Apex*.—Acute.

*Base*.—Obtuse.

*Margin*.—Entire.

*Texture*.—Upper and lower surfaces: Smooth.

*Venation pattern*.—Parallel.

*Color*.—Immature leaves: Upper surface: RHS 144A. Lower surface: RHS 146C. Mature leaves: Upper surfaces: RHS 137A. Lower surface: RHS 137C. Venation: RHS 137A.

Flower description:

*Flower type and habit*.—Double, round, small sprays.

*Fragrance*.—Present.

*Natural flowering season*.—Spring to fall.

*Flower longevity*.—10 to 12 days.

*Number of flowers per spray*.—3-5.

*Position of the flowers when compared to the foliage*.—Far above.

*Flower buds*.—Length: 2.0 cm to 2.4 cm. Diameter: 1.0 cm. Shape: Oval. Color: RHS 143A, RHS 143C, RHS 137C and RHS 176A. Extrusion of the styles at bud stage: Absent.

*Corolla*.—Quantity of petals/arrangement: Greater than 20, arranged in several whorls. Corolla height: 1.8 cm to 2.0 cm. Petal length: 4.0 cm. Petal width: 1.8 cm to 2.0 cm. Petal shape: Spoon shaped. Petal apex: Obtuse. Petal base: Acute. Petal margin: Crenate. Depth of petal margin: Medium. Petal texture: Upper and lower surfaces: Satiny. Petal color: Immature: Upper surface: RHS 46B. Lower surface: RHS 47B. Mature: Upper surface: RHS 53C. Lower surface: RHS 56A. Calyx: Quantity of sepals/arrangement: 4 to 5, fused. Calyx height: 2.0 cm. Calyx diameter, at the apex: 1.0 cm to 1.2 cm. Calyx shape: Campanulate. Sepal texture: Upper and lower surfaces: Smooth. Sepal color: Upper surface: RHS 144A. Lower surface: RHS 145C.

Peduncles:

*Length*.—16.0 cm to 18.0 cm.

*Diameter*.—0.2 cm.

*Strength*.—Moderate.

*Texture*.—Smooth.

*Color*.—RHS 137.

Reproductive organs:

*Stamens*.—Quantity: 3 to 5. Filament length: 0.3 cm to 0.5 cm. Filament color: RHS 158D. Anther length: 0.2 cm. Anther diameter: 0.1 cm. Anther color: RHS 158A. Pollen amount: Sparse.

*Pistils*.—Quantity: 1. Pistil length: 0.1 cm. Style length: 2.5 cm. Style color: RHS 155B. Stigma shape: Filamentous. Stigma color: RHS 60A. Ovary size: 0.6 cm. Ovary shape: Oval. Ovary color: RHS 145A.

*Fruits/seeds*.—Seed sometimes observed but additional information on seed description is not available.

Disease and insect/pest resistance: No special observations were made.

COMPARISON WITH PARENTAL LINES AND KNOWN VARIETY

'KLEDP13155' is a distinct variety of *dianthus*. 'KLEDP13155' is distinguished from its parents as described in Table 1:

TABLE 1

Comparison with Parental Lines

| Trait | Variety 'KLEDP13155' | Female parent 'DCP 2007 0056' | Male Parent 'Fire' |
|---|---|---|---|
| Branching | Good | Less branching | Medium |
| Vigor | Strong | Medium | Medium |

'KLEDP13155' is most similar to the commercial *dianthus* plant named SuperTrouper 'Benita' (unpatented). Differences between the two varieties are described in Table 2:

TABLE 2

Comparison with Similar Variety

| Trait | Variety 'KLEDP13155' | Commercial line SuperTrouper 'Benita' |
|---|---|---|
| Ray florets color and stability | Shiny red, stable | Unstable color |

We claim:

1. A new and distinct variety of *Dianthus* plant named 'KLEDP13155' as illustrated and described herein.

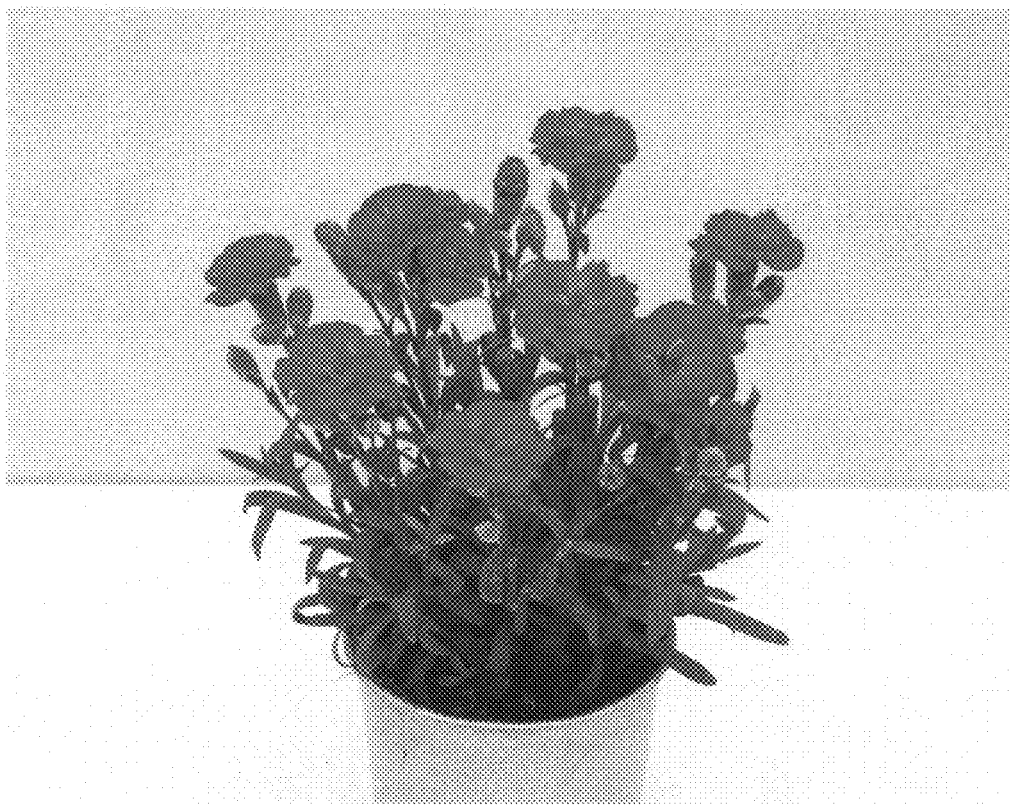

* * * * *